United States Patent [19]

Bazterrica et al.

[11] Patent Number: 5,063,065

[45] Date of Patent: Nov. 5, 1991

[54] COMPOSITION AND METHOD FOR THE TREATMENT OF GENITAL DYSPLASIA

[76] Inventors: Enrique J. V. Bazterrica; Enrique T. V. Bazterrica, both of 266 Roque Saenz Pena St., 1st Fl. "E" (1642), San Isidro, Province of Buenos Aires, Argentina

[21] Appl. No.: 594,838

[22] Filed: Oct. 9, 1990

[51] Int. Cl.$^5$ .............................................. A61K 33/34
[52] U.S. Cl. ..................................................... 424/637
[58] Field of Search ......................................... 424/637

[56] References Cited

PUBLICATIONS

Chem. Abst. 112 (1990)–43584s–Ref to 1989 article.

*Primary Examiner*—Stanley J. Friedman
*Attorney, Agent, or Firm*—Ladas & Parry

[57] ABSTRACT

The invention relates to a pharmaceutical composition comprising copper sulfate as active agent which is effective for the diagnosis and treatment of genital dysplasia associated with viral condylomatosis.

The invention also relates to a method for treating patients with the copper sulfate composition of the invention for detecting the existence of genital dysplasia and for curing such abnormality in the human organism.

3 Claims, No Drawings

COMPOSITION AND METHOD FOR THE TREATMENT OF GENITAL DYSPLASIA

FIELD OF THE INVENTION

This invention pertains to the field of gynecology and urology and refers more specifically to a pharmaceutical composition which is effective for diagnosing and treating genital disorders, in particular dysplasia associated with viral condylomatosis.

The invention refers in addition to the use of the novel composition in a method in which a patient is treated with the composition for the purpose of detecting the existence of genital dysplasia and/or curing such disorder in the human organism.

The composition of this invention comprises a saturated solution of copper sulfate in distilled water or in glycerine. It is also possible to associate the copper sulfate with a 2% lidocaine hydrochloride solution as a local contact anesthetic.

The contact of copper sulfate with the affected area has shown to be effective for the detection and thereafter the cure of viral infections in the mucous membrane of the male and female genital tract. The detection and cure is obtained by the mere contact of the copper sulfate composition with the infected tissue.

DESCRIPTION OF THE PRIOR ART

A number of methods and techniques are known in the art for the diagnosis and treatment of genital dysplasia.

Chemical treatments with 50% podophyllin solution in Siam benzoin, 50% trichloracetic acid which must be made precisely over the damaged zone without extending to the surrounding tissue in view of the highly caustic effect of the substances applied. Its usefulness is thus limited to small and accessible wounds. This technique also has no possibility of being self applied. Furthermore, when the application of these substances is extended to the base membrane they leave scars, depending on the concentration and number of applications.

Treatment with heat generated by electricity, such as electrodiathermo-coagulation, Cartier's loop, electrocauterization, etc.

The zone in which this treatment may be applied is limited in view of the effects it generates. It is not very effective because due to precautionary reasons this technique cannot be intensively applied. So doing may produce adverse effects such as retractile scars.

When treating the neck of the uterus and as a result of the scars which are generated, if these are retractile, a carcinoma may remain hidden in the neck or may be generated subsequently.

Very low temperature coagulation, such as cryosurgery and cryocoagulation. This technique also must be applied to small affected areas. Otherwise, it may produce coagulation of inner tissues and subsequently scars. It furthermore requires specific equipment and elements for its application. Because its application is local it has no favorable effect over other infected areas and due to its relatively high cost this technique is limited to particular cases.

Laser vaporization shows the same features as cryosurgery and has the same disadvantages. It requires an equipment of even greater complexity and more skilled personnel with a resulting increase in cost, all of which limits even more its usefulness. It must also be noted that this technique implies a risk for the persons who apply it, in terms of virus aspiration, photocoagulation, etc.

Antineoplasies, such as 5-fluoroacyl cream, bleomycin cream: Most of the physicians agree in that these substances are therapeutically ineffective and have a great tendency of producing inflammatory wounds in healthy tissue. It is also costly.

Interferon: The application of this substance is very expensive and requires the application by means of injection in each affected zone with high weekly frequency during an extended period of time of up to several months. The results are questionable.

Surgery: Ablation of the infected tissue is exclusively by means of the application of laser-ray for this purpose or also by means of the classical resection surgery, with general or local anesthesia. The disadvantages of this technique are the risks of causing mutilation, infertility, sterility. It involves a high cost due to the highly specialized equipment required, skilled personnel, hospitalization, etc. It furthermore fails to assure a definitive cure.

In view of the foregoing, it would be highly advantageous if a product could be found leading to a more effective diagnosis, treatment and cure of genital dysplasia in general and which furthermore can be applied by a method which is less complicated and hazardous. This invention provides such a product and method as herein disclosed.

DETAILED DESCRIPTION OF THE INVENTION

The use of copper sulfate according to this invention is based on studies carried out in experimental medicine and clinical investigation in the treatment of genital dysplasia associated with viral condylomatosis in human beings.

In a first embodiment, the copper sulfate composition of this invention, when applied to the genital zone under study enables the clear observation of viral condylomas, including those infected zones which cannot be detected by means of the diagnostic methodologies known up to now, which furthermore are rarely specific.

In a second embodiment, by means of the appropriate administration of the composition of this invention, it is possible to obtain the necrosis of infected tissue, which a few hours later separates itself without seemingly affecting the base membrane. As a result, the restoration of the affected zone occurs in a short time of about one week without leaving any kind of scars.

It must be stressed that with the use of the composition of this invention the neighboring tissues are never in any way affected, that is they are not destroyed or stained.

The composition of this application is prepared by simply mixing the copper sulfate with a vehicle selected from water, glycerine and a 2% lidocaine hydrochloride solution until the vehicle becomes saturated with the copper sulfate.

The method of use of the composition comprises its application locally over the external genital organ. After the first application, the treatment is repeated 24 and 96 hours afterwards in the same manner. Three basic applications have been sufficient to obtain the disappearance of dysplasia in its different degrees of evolution and localization. Not so the viroses which in some case appear to persist. Their eradication would depend of other surrounding factors such as reinfections, immunological factors, etc.

The copper sulfate composition of this invention has shown to be therapeutically effective for detecting and curing dysplasias of the genital tract when associated to infections by human virus papiloma. Remission of non-dysplasic lesions caused by human virus papiloma have been observed.

Because the composition acts exclusively on the infected tissue it produces no structural damage to the internal tissues and the skin so that no scars are left, regardless of the concentration and frequency of application.

The treatment with the composition is harmless because it is applied locally and its action is limited to the areas affected by human virus papiloma, with or without dysplasia alterations.

The use of the composition for diagnostic purposes has enabled the detection of lesions which go unnoticed by the usual diagnostic procedures applied, except biopsy.

The manner of applying the composition is simple and may be carried out topically even by the patient himself in the form of pads, creams, gels, etc. No specific equipment or installation is thus required for its application.

No side effects have been observed to occur and in case of reinfection or relapse the treatment may be repeated without losing its high degree of innocuousness.

It should finally be noted that the active component of the composition and the carriers are all common and known such that the cost of the treatment is accessible to all levels.

CLINICAL TRIALS

The following are two clinical trials where copper sulfate was shown to be effective when applied to patients suffering from genital dysplasia:

Case 1

A 21 year old female patient suffering from cervical condylomatosis was treated by means of electrocoagulation of the neck of the uterus. A year after, due to the persistence of the disorder, the patient was treated by cryocoagulation of the uterine neck and six months afterwards, the treatment continued by applying laser-rays to the uterine neck, vagina and vulva. The next year byopsy of the neck and vulva revealed the persistence of the virosis and as a result topical treatment with silver nitrate was applied. The following year, laser-ray treatment was repeated on the vulva and uterine neck whereby moderate dysplasia was detected. That same year partial vulvectomy was practiced removing the upper left labium.

The process still persisted so fifteen applications with 5-fluoroacyl cream were made a few months afterwards.

Two months later treatment with the copper sulfate composition of this invention was started. The first application consisted of vulval, vaginal and cervical topical applications. In a few minutes, an intense bluish-green staining was observed in areas of the uterine neck, vagina and particularly the major labium in its left parauretal zone. A second application some days after resulted in lesions with high degree of congestion, separation and ardor sensation. The following day stained lesions disappeared and congestive zones were no longer stained when contacted with the copper sulfate composition of the invention. That same day a third cure with 50% copper sulfate solution was made.

A control five days later showed a total absence of genital lesions and there were no discomforts. A further asymptomatic application was effected.

A week later there was an absence of lesions and the tissue restoration was observed. When topical treatment was effected no staining occurred nor local discomforts. The cure was regarded complete. A byopsy of the vulva was effected as a control. Eight days later the byopsy revealed the disappearance of dysplasia, the absence of symptomatology and incipient condylomatosis lesions.

A control the day after showed the absence of all discomforts. The application of the composition caused no staining nor local discomforts. Three days later a new byopsy control of the upper labium of the vulva revealed the total absence of valvular lesions. The cure of the dysplasia and the disappearance of the genital virosis was established and the patient was declared cured.

Case 2

A 40 years old man started suffering of discomforts in the glans with ardor and pruritus. A byopsy of the penis was effected and the diagnosis was genital dysplasia with simultaneous viral action. Treatment with laser-rays was recommended but not carried out. Eight applications with 5-fluoroacyl cream were made.

The following year a second byopsy was made and the diagnosis was moderate dysplasia and epithelial lesions due to human virus papiloma.

Three months later the patient shows congestive parauretal lesions of the glans. At this time treatment with the composition of this invention is initiated on the basis of copper sulfate solution applied topically over the entire penis. In 24 hours there is evidence of a number of lesions which are stained with a greenish-blue shade over paraureteral ulcerations and all over a stain in the superior face of the glans. The tissue started to loosen and separate. A second application with the copper sulfate solution was effected.

A control two days after showed persistent congestive lesions but with complete separation of the affected tissue. The well defined lesions reveal a wrinkled and whitish halo, sensible to the touch. Thereafter, the third application with the solution is effected. No staining is observed.

Two days later a control shows the absence of discomforts and the total disappearance of lesions. A new tissue with normal characters has replaced the old. With a fourth application of the solution there are no lesions stained nor does it provoke local discomfort. The patient is regarded cured and declared to be in sound condition.

It should be understood that what has been described herein is only for illustrative purpose and that various modifications and changes in the light thereof will be suggested to persons skilled in the art and are to be included within the spirit and purview of this application and the scope of the appended claims.

We claim:

1. A method for the diagnosis of genital dysplasia associated with viral condylomatosis, comprising applying an effective amount of a composition comprising a saturated solution of copper sulfate in a pharmacological acceptable medium to an area where genital dysplasia is suspected and observing the area for staining.

2. A method for treating patients suffering from genital dysplasia associated with viral condylomatosis, comprising applying an effective amount of a composition comprising a saturated solution of copper sulfate in a pharmacologically acceptable medium to an infected area.

3. A composition for the diagnosis and treatment of genital dysplasia associated with viral condylomatosis comprising a saturated solution of copper sulfate in a pharmacologically acceptable medium selected from the group consisting of glycerine and 2% lidocaine hydrochloride solution.

* * * * *